United States Patent [19]

Meador

[11] 4,087,937

[45] May 9, 1978

[54] APPARATUS FOR POLLENATING PLANTS

[76] Inventor: Lawrence Dean Meador, R.R. 2, Lanark, Ill. 61046

[21] Appl. No.: 811,626

[22] Filed: Jun. 30, 1977

[51] Int. Cl.² ............................................. A01G 7/00
[52] U.S. Cl. ................................................... 47/1.41
[58] Field of Search .............................. 47/1, 1.41, 1.7

[56] References Cited

U.S. PATENT DOCUMENTS

| 1,864,198 | 6/1932 | Johnson | 47/1.41 X |
| 2,570,511 | 10/1951 | Blair | 47/1.41 |
| 2,685,149 | 8/1954 | Hvistendahl | 47/1.41 |

FOREIGN PATENT DOCUMENTS

| 550,728 | 5/1932 | Germany | 47/1.41 |
| 400,287 | 3/1974 | U.S.S.R. | 47/1.41 |
| 490,438 | 2/1976 | U.S.S.R. | 47/1.41 |

*Primary Examiner*—Robert E. Bagwill
*Attorney, Agent, or Firm*—Leydig, Voit, Osann, Mayer & Holt, Ltd.

[57] ABSTRACT

Pollen from rows of male seed corn is shaken loose therefrom, is sucked upwardly into a shroud and then is blown into two manifolds which extend transversely from opposite sides of the shroud. Several hoses depend from the manifolds and distribute the pollen uniformly into rows of female corn, the female rows being located on opposite sides of the male rows.

18 Claims, 6 Drawing Figures

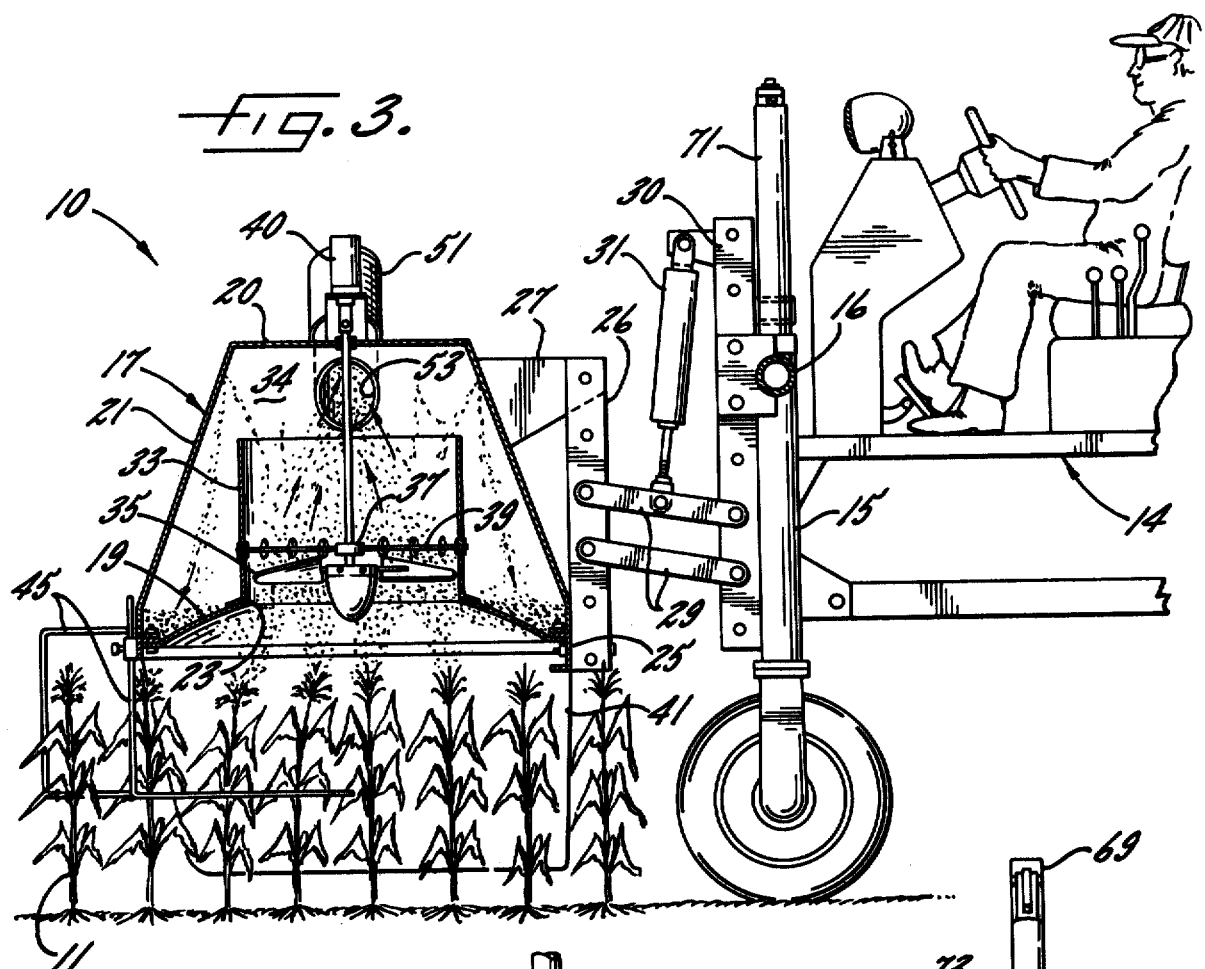
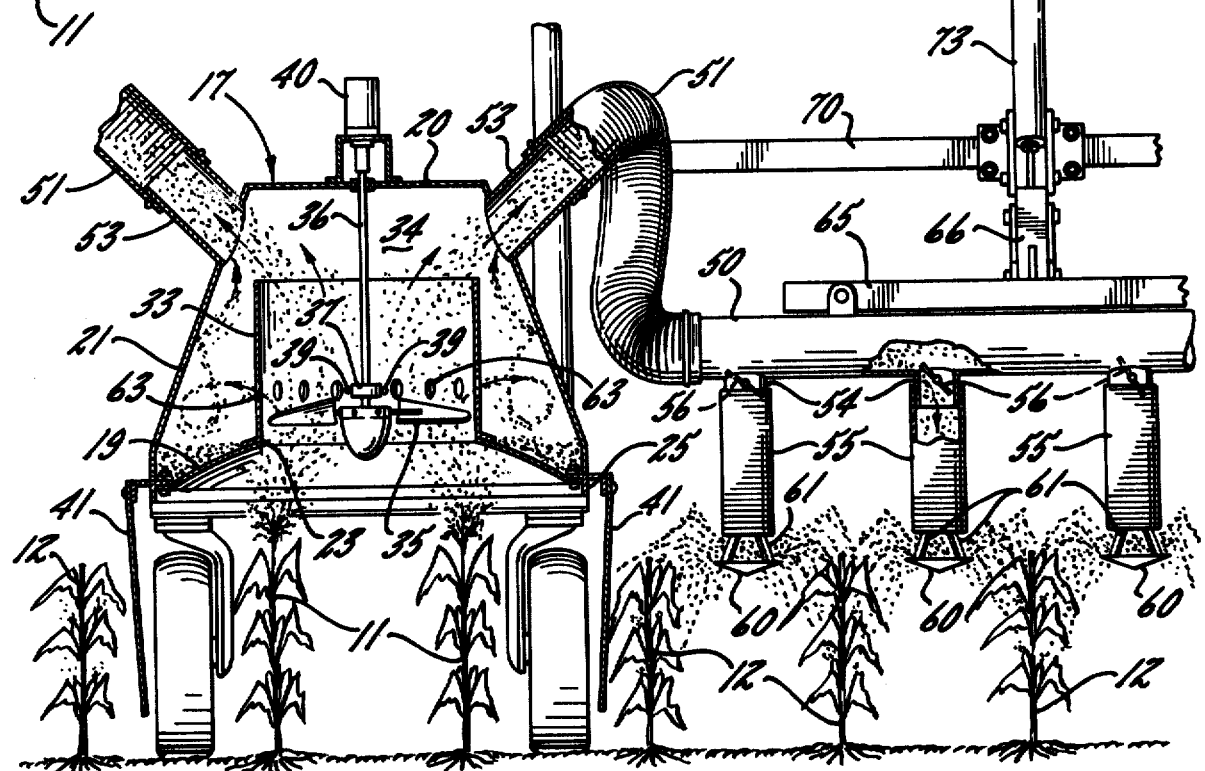

APPARATUS FOR POLLENATING PLANTS

BACKGROUND OF THE INVENTION

This invention relates to apparatus for pollenating plants and, more particularly, to apparatus for pollenating single cross hybrid seed corn.

In the production of single cross hybrid seed corn, it is standard practice to plant several rows of female corn on opposite sides of one or more rows of male corn, the stalks of the male corn having tassels with pods which contain pollen. The tassels of the stalks of the female corn are cut away and such corn is pollenated by spreading the pollen from the pods of the male corn onto the silk of the ears of the female corn.

Heretofore, the pollen from the pods of the male corn most usually has been transferred to the silk of the female corn by relying on wind or insects to carry the pollen, by using the propeller wash from an airplane to stir and distribute the pollen or by hand bagging and manually spreading the pollen. Hand bagging requires considerable labor and the other methods are relatively inefficient because much of the pollen simply falls to the ground rather than being deposited onto the female corn and because it is difficult to obtain pollenation at the proper time.

SUMMARY OF THE INVENTION

The general aim of the present invention is to provide new and improved apparatus for pollenating plants such as seed corn in a simpler and more efficient manner than has been possible in the past, the apparatus positively picking up the pollen from the male plants and distributing the pollen gently, evenly and at the correct height on the female plants.

A more detailed object of the invention is to achieve the foregoing by providing apparatus which sucks the pollen upwardly from the male plants and then blows such pollen downwardly onto several rows of female plants located on opposite sides of the male plants.

Still another object is to provide apparatus which is capable of shaking the male plants to positively release the pollen therefrom and thereby insure that a large percentage of the pollen will be sucked upwardly from the male plants.

In a more specific sense, the invention resides in the provision of a machine having a chamber for sucking the pollen upwardly from the male plants and having transversely extending manifolds communicating with the chamber and adapted to distribute the pollen uniformly onto several rows of female plants.

A further object of the invention is to provide a machine of the foregoing character in which the working elevation of the chamber and the manifolds may be adjusted as necessary to accommodate plants of different heights.

These and other objects and advantages of the invention will become more apparent from the following detailed description when taken in conjunction with the accompanying drawings.

BRIEF DESCRIPTION OF THE DRAWINGS

FIGS. 3, 4 and 5 are fragmentary cross-sections taken substantially along the lines 3—3, 4—4 and 5—5, respectively, of FIG. 2.

DETAILED DESCRIPTION OF THE PREFERRED EMBODIMENT

Figure 1:
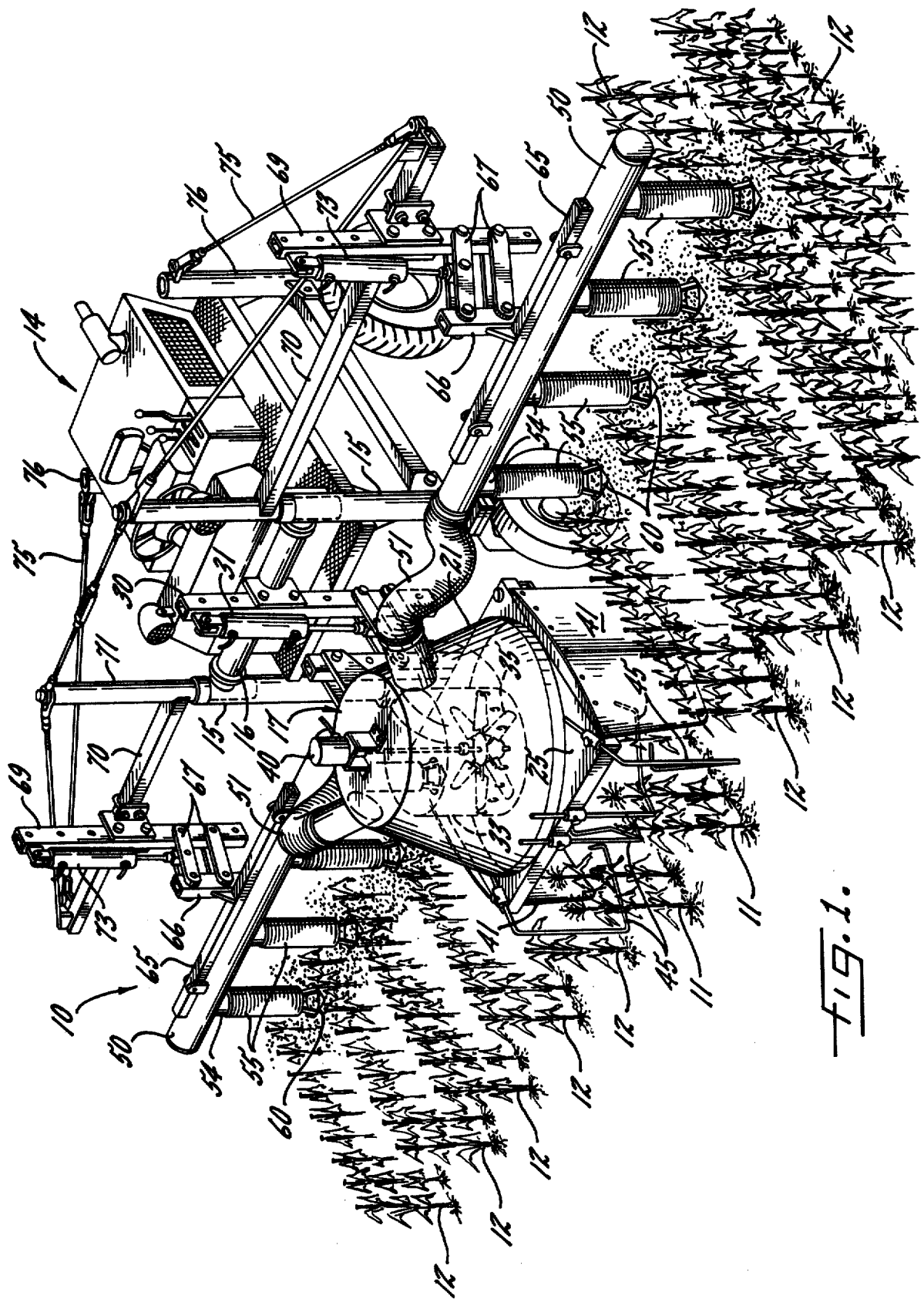
FIG. 1 is a perspective view of new and improved pollenating apparatus incorporating the unique features of the present invention and shows the apparatus attached to a typical farm tractor.

As shown in the drawings for purposes of illustration, the invention is embodied in a machine 10 for pollenating plants such as single cross hybrid seed corn. In the seed corn field which has been illustrated, at least one and preferably two rows 11 of male corn are centered between several rows 12 of female corn, there herein being five rows of female corn located on each side of the two male rows. As is conventional in a field of this type, the tassels of the stalks of the female rows 12 are cut off or otherwise removed and thus the female stalks are somewhat shorter than the male stalks (see FIG. 4).

The tassels of the stalks of the male rows 11 include pods which become filled with grains of pollen at a particular time in the growing season. Pollenation of the female rows 12 is effected when the pollen grains are transferred from the pods of the male rows and are deposited onto the silks of the ears of the female rows. Most efficient use of the pollen is achieved when the pollen is transferred in such a manner that only a relatively small number of male rows is required to effectively pollenate a comparatively large number of female rows.

The present invention contemplates a new and improved machine 10 which efficiently transfers the pollen by positively picking up the pollen from one or more male rows 11 and then by distributing such pollen in a positive and substantially uniform manner onto several female rows 12 located on opposite sides of the male row or rows. As a result of the machine positively picking up and distributing the pollen, the pollen is transferred in a simpler, more reliable and more effective manner than has been possible heretofore.

In the present instance, the pollenating machine 10 is mounted on the front of a suitable farm vehicle 14 such as a Model 470 H Hagie High Boy Tractor. A tractor of this type includes a pair of vertically extending and transversely spaced tubes 15 at its forward end, the tubes being spanned by a transversely extending rod 16.

In carrying out the invention, the pollen from the male rows 11 is sucked upwardly therefrom and is drawn into a shroud 17 prior to being blown downwardly onto the female rows 12. The shroud preferably is defined by a frusto-conical dome having a bottom wall 19 (FIG. 3), a horizontal top wall 20 and an annular side wall 21 which tapers inwardly upon progressing upwardly. The bottom wall 19 has a concave lower side and a convex upper side and is formed with a central opening 23 whose diameter is approximately equal to the spacing between the two rows 11 of male corn (see FIG. 4). An apertured platform 25 (FIG. 1) of rectangular shape extends around the bottom wall 19 and supports an upstanding channel 26 (FIG. 3) whose upper end portion is connected to the side wall 21 by ears 27 which extend rearwardly from the side wall. Upper and lower pairs of parallel links 29 are pivotally connected to the channel 26 and to a similar upright channel 30 which is secured to the tansverse rod 16 of the tractor 14. A hydraulic actuator 31 is connected between the upper links 29 and the channel 30 and may be operated to adjust the shroud 17 vertically to a position in which the bottom wall 19 and the platform 25 are located just above the tassels of the male rows 11.

The shroud 17 is completed by an upright sleeve or cylinder 33 (FIG. 3) having open upper and lower ends and located just above the bottom wall 19 of the shroud. The cylinder is welded to the bottom wall and is positioned with its lower end alined with the opening 23 in the bottom wall and with its upper end spaced well below the top wall 20 of the shroud. Thus, the cylinder 33 and the walls 20, 21 and 23 of the shroud 17 coact to define a downwardly opening chamber 34 which overlies the two male rows 11 as shown in FIG. 4.

Means are provided for creating a negative pressure in the shroud 17 so that the pollen of the male rows 11 will be sucked upwardly therefrom and will be drawn into the shroud as the latter is moved along the rows by the tractor 14. Herein, these means comprise an axial fan 35 (FIG. 3) located within the cylinder 33 adjacent the lower end thereof and fastened to the lower end of a vertical shaft 36. The upper end portion of the shaft is journaled in the top wall 20 of the shroud while the lower end portion of the shaft is supported by a bearing 37 which is secured between two rods 39 extending across the cylinder 33. A hydraulic motor 40 is supported on the top wall 20 of the shroud and is connected to the upper end of the shaft 36.

When the motor 40 is operated, the fan 35 is rotated in a direction to create a very strong upward draft within the shroud 17 and in the area beneath the bottom wall 19. Accordingly, the pollen from the male rows 11 underlying the shroud is sucked upwardly into the cylinder 33 and passes into the chamber 34. To enable the suction created by the fan to act effectively on the pollen of the male rows, flexible skirts or flaps 41 (FIGS. 1 and 4) are secured to and depend from opposite transverse sides of the platform 25 and straddle opposite sides of the two male rows so as to help confine the suction to those rows.

Importantly, shakers 45 (FIGS. 1 and 2) are located beneath the shroud 17 and deflect or whip the stalks of the male rows 11 back and forth in a transverse direction just prior to and during the time the shroud passes over the stalks. As a result of such whipping, the pollen pods are opened and the pollen is shook loose from the pods so that a greater amount of pollen is sucked into the chamber 34.

More specifically, one pair of shakers 45 is provided for each row 11 of male corn, the shakers of the pair straddling opposite sides of the row. Each shaker is in the form of a rod having an upper end portion which is suitably secured to the platform 25. The lower end portions of the shakers are disposed in a horizontal plane about midway along the height of the male stalks and are suitably bent so that a serpentine throat is defined between the shakers of each pair (see FIG. 2). Thus, the shakers whip the male stalks transversely as the shakers move along opposite sides of the stalks and, as a result, the pollen in the pods is loosened and may be more easily sucked from the pods.

In carrying out the invention, the pollen which is sucked into the shroud 17 is blown into two manifolds 50 extending transversely from opposite sides of the shroud and then is blown downwardly onto the female rows 12 of corn. Each manifold is in the form of an elongated rigid pipe whose outer end is closed and whose inner end is connected to a flexible pipe or hose 51. The latter, in turn, is connected to a metal duct 53 (FIG. 4) which extends upwardly and outwardly from the side wall 21 of the shroud 17 and which communicates with the chamber 34.

Figure 5:
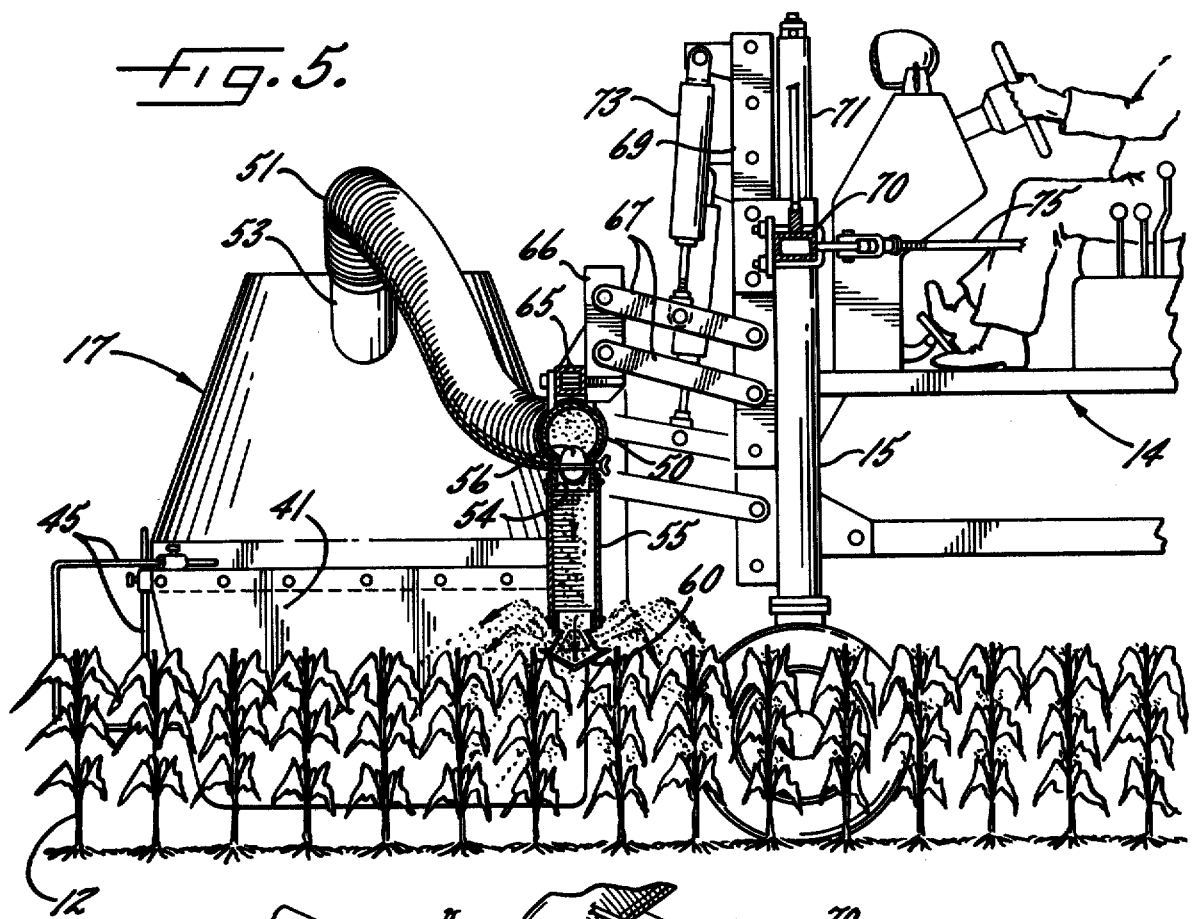

Four metal ducts 54 (FIGS. 4 and 5) are spaced transversely along and depend from each manifold 50 and communicate with the interior thereof. Connected to the lower end of each duct 54 is a flexible conduit or hose 55 having an open lower end. Each hose is positioned transversely along the manifold so as to be located between two female rows 12 of corn. In addition, the lower end of each hose is located closely adjacent the upper ends of the stalks of the female rows (see FIG. 5).

When the fan 35 is operated, the pollen which is sucked into the chamber 34 is blown outwardly through the manifolds 50 and then is blown downwardly through the hoses 55. To help maintain a substantially uniform flow rate through all of the hoses of each manifold, manually adjustable flapper valves 56 (FIGS. 4 and 5) are located in the upright ducts 54 and may be set in different positions so as to throttle the hoses to progressively lesser degrees as the hoses progress outwardly.

In order to promote uniform distribution of the pollen on both of the female rows 12 between which each hose 55 is located, a unique diffuser 60 (FIGS. 4 and 5) is located at the lower end of each hose. Herein, each diffuser is in the form of an inverted conical dish and is connected to the lower end of its hose 55 by angularly spaced straps 61. Upon being discharged from the hose, the pollen strikes the diffuser, bounces upwardly out of the diffuser and then floats downwardly onto the female rows in the form of an umbrella-shaped cloud (see FIG. 5). Accordingly, the pollen which is discharged from each hose 55 is dispensed into a wide circular pattern by the underlying diffuser 60 so that the pollen may settle uniformly onto the silks of the adjacent female rows. Although the inner side of each innermost female row is not directly adjacent a diffuser, such side, —being close to a male row 11— usually is adequately pollenated by the natural action of wind and insects.

Under certain conditions, insects may attack the corn of the male rows 11 and cause some of the tassels to become sticky so that little or no pollen is sucked up into the chamber 34 from those particular stalks in the male rows. To avoid the risk of leaving some of the corn of the female rows 12 unpollenated if there is not an immediate supply of pollen from the male rows, provision is made to temporarily conserve and transport some of the pollen which is obtained from the male rows. For this purpose, several angularly spaced openings or slots 63 (FIG. 4) are formed in the cylinder 33 just above the fan 35. When the latter is rotated, some of the pollen passes through the slots and is temporarily collected in the space which is adjacent the junction of the bottom wall 19 and the side wall 21 of the shroud 17 rather than being immediately blown into the manifolds 50. If there is not an immediate supply of pollen from the male rows, the collected pollen is discharged into the manifolds so as to pollenate the female rows.

Advantageously, the elevation of the two manifolds 50 may be adjusted relative to the shroud 17 so that the manifolds and the hoses 55 may be set at the proper height with respect to the female rows 12. Also, each manifold may be vertically adjusted independently of the other manifold so as to enable the manifolds to be set at different heights if, for example, the machine 10 is moving along the side of a hill.

To these ends, a horizontal channel 65 (FIG. 1) is attached to the upper side of each manifold 50 and supports an upright channel 66. The latter is connected by upper and lower pairs of pivoted parallel links 67 to another upright channel 69 which is connected to the outer end portion of a horizontal outrigger 70. The inner end of each outrigger is connected to a vertical post 71 which is rotatably supported within the adjacent tube 15 of the tractor 14.

An hydraulic actuator 73 (FIG. 1) is connected between each upright channel 69 and the upper links 67 of each set. By operating the actuators, each manifold 50 may be adjusted vertically relative to the shroud 17 and relative to the other manifold so as to set the discharge hoses 55 at the proper working height.

Figure 2:
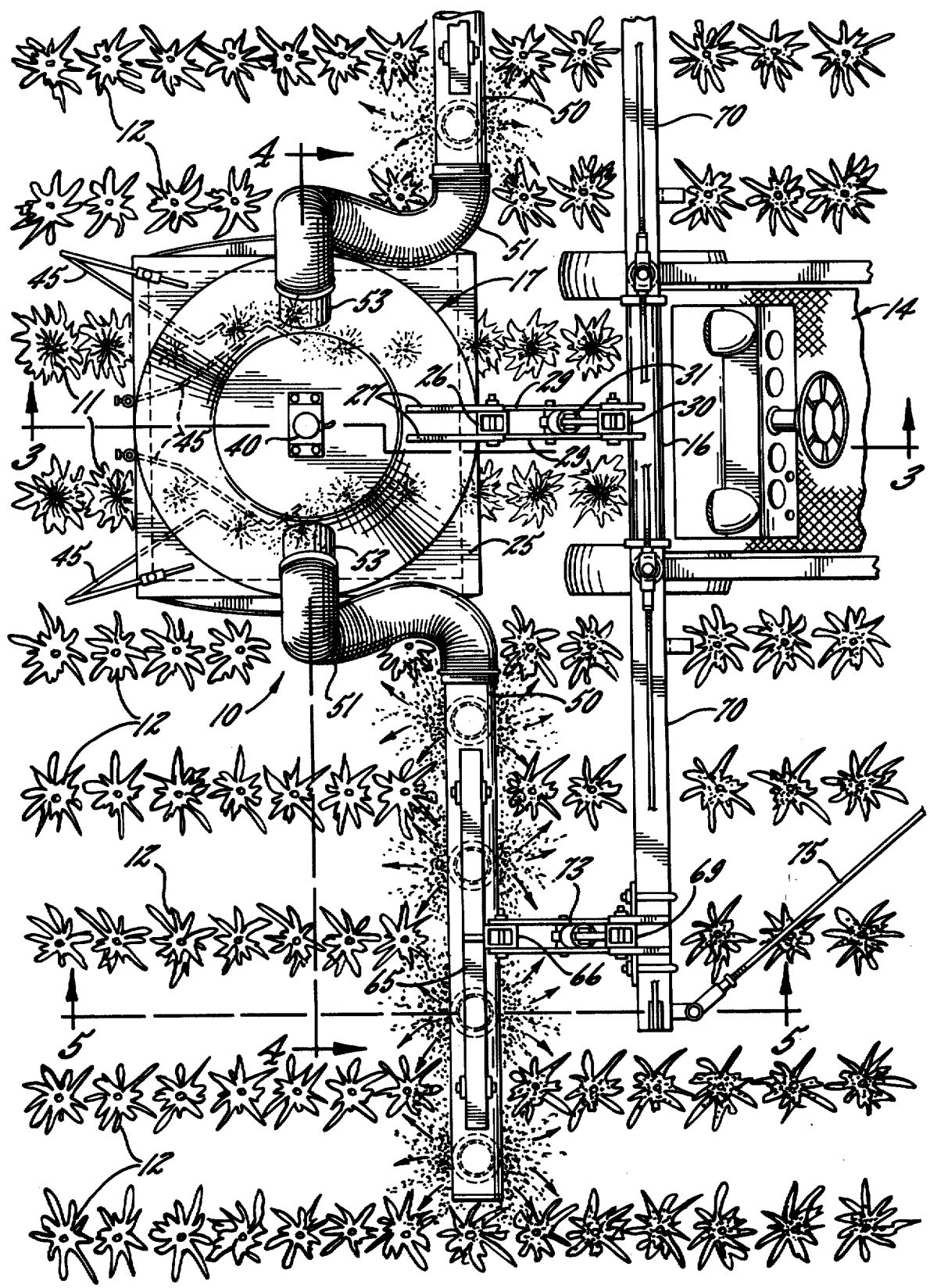
FIG. 2 is an enlarged fragmentary top plan view of the pollenating apparatus and tractor shown in FIG. 1.
Figure 6:
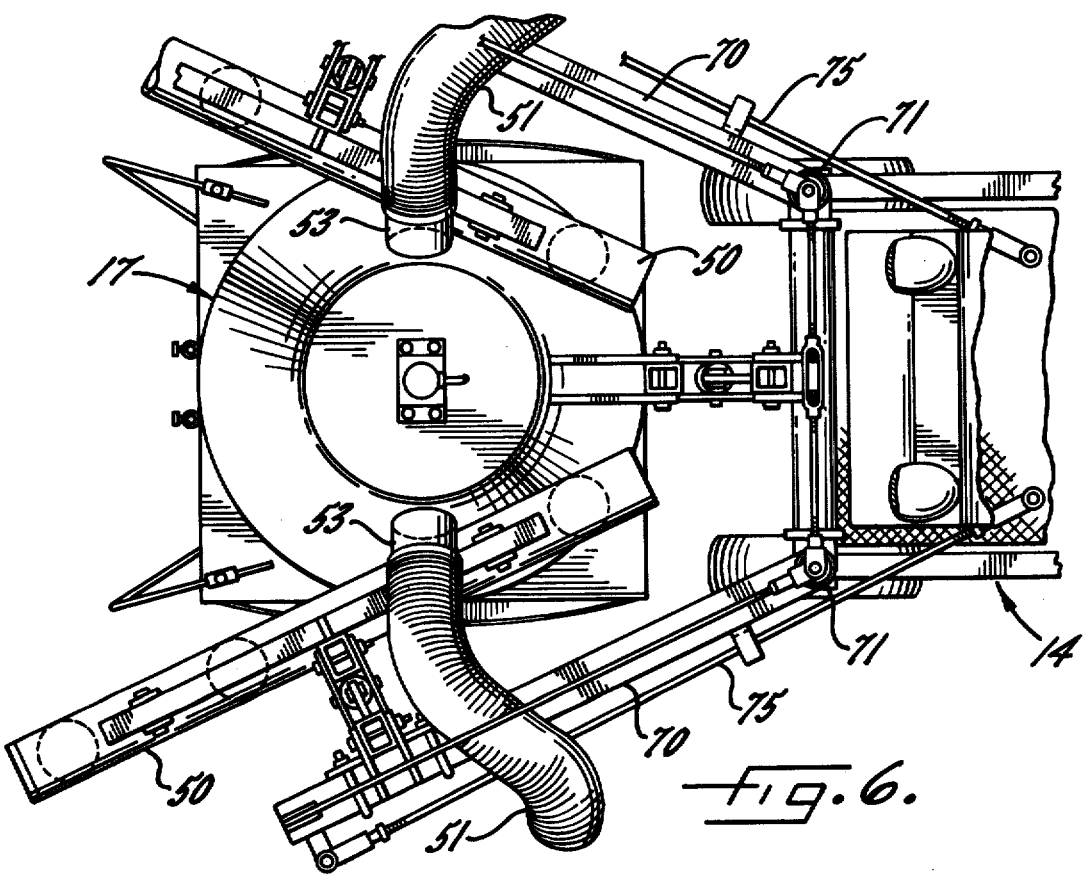
FIG. 6 is a fragmentary top plan view similar to FIG. 2 and shows certain parts of the apparatus in moved positions.

Each manifold 50 also may be swung to a transport position in which the manifold extends in a generally fore-and-aft direction to enable the machine 10 and the tractor 14 to travel along a road or highway. As shown in FIG. 1, each manifold 50 normally is held in its transversely extending position by a strut 75 which is connected to the outer end of the respective outrigger 70 and to a rear tube 76 on the tractor. By disconnecting the strut 75 from the tube 76 and by disconnecting the hose 51 from the inner end of the manifold 50, the post 71 may be rotated within the tube 15 to cause the manifold and the outrigger 70 to swing forwardly to the transport position shown in FIG. 6.

From the foregoing, it will be apparent that the present invention brings to the art a new and improved machine 10 for effectively pollenating rows 12 of female seed corn even though such rows are located a substantial distance from the male rows 11. The machine is particularly characterized by the fact that the pollen is shaken loose from the male rows just prior to being subjected to the suction and then is diffused uniformly onto the female rows as an incident to being discharged from the hoses 55.

I claim:

1. Apparatus for transferring pollen from a first row of plants to second and third rows of plants located on opposite sides of said first row, said apparatus comprising a shroud adapted for attachment to a vehicle and defining a downwardly opening chamber, said chamber overlying said first row as said vehicle moves along said rows, downwardly opening conduits located on opposite sides of said shroud and positioned adjacent said second and third rows, means establishing communication between said conduits and said chamber, and means for sucking pollen upwardly from said first row and into said chamber and for blowing such pollen through said conduits and downwardly onto said second and third rows.

2. Apparatus as defined in claim 1 in which said shroud comprises a dome having top and bottom walls and having an annular side wall extending between said top and bottom walls, said side wall tapering inwardly upon progressing upwardly, said shroud further comprising an upright sleeve disposed within said dome and having an open upper end spaced below the top wall of said dome, said sleeve having an open lower end communicating with an opening in the bottom wall of said dome, and said sucking and blowing means comprising a fan disposed within said sleeve and further comprising a motor for rotating said fan about an upright axis.

3. Apparatus as defined in claim 2 in which several angularly spaced openings are formed through said sleeve, said openings being located above said fan.

4. Apparatus as defined in claim 2 in which each of said conduits comprises an upright piece of flexible hose, said communication establishing means comprising (a) a rigid horizontal pipe connected to the upper end of each conduit and (b) a flexible pipe connected to the inboard end of each rigid pipe and communicating with said dome through the side wall thereof.

5. Apparatus as defined in claim 1 further including a pair of plant shakers located beneath said shroud and positioned to straddle the plants of said first row, said shakers deflecting the plants of said first row back and forth in a substantially transverse direction as said shroud is moved along said first row whereby pollen on the plants of said first row is loosened from such plants and then is sucked into said chamber.

6. Apparatus as defined in claim 1 further including means for selectively adjusting the elevation of said shroud relative to said vehicle, and means for selectively adjusting the elevation of said conduits relative to said shroud.

7. Apparatus as defined in claim 6 in which said last-mentioned means includes a first actuator connected to one of said conduits and a second actuator connected to the other of said conduits, said actuators being operable independently of one another to enable the elevation of said one conduit to be adjusted relative to the elevation of said other conduit.

8. Apparatus for transferring pollen from a center row of plants to at least three outboard rows of plants on the left side of said center row and to at least three additional outboard rows of plants on the right side of said center row, said apparatus comprising a shroud adapted for attachment to a vehicle and defining a downwardly opening chamber, said chamber overlying said center row as said vehicle moves along said rows, a pair of plant shakers located beneath said shroud and positioned to straddle the plants of said center row, said shakers deflecting the plants of said center row back and forth in a substantially transverse direction as said shroud is moved along said center row whereby pollen on the plants of said center row is loosened from such plants, substantially horizontal manifolds extending transversely from the left and right sides of said shroud and communicating with said chamber, a pair of upright conduits depending from and communicating with each of said manifolds and each having an open lower end, each manifold having one of its conduits located between the first and second rows of the respective outboard rows and having the other of its conduits located between the second and third rows of the respective outboard rows, means for sucking pollen upwardly from said center row and into said chamber and for blowing such pollen through said manifolds and said conduits, and means adjacent the lower end of each conduit for diffusing the pollen blown through the conduit and for spreading such pollen onto the rows between which the conduit is located.

9. Apparatus as defined in claim 8 in which each of said diffusing means is an inverted conical dish, each dish being spaced below the lower end of the respective conduit.

10. Apparatus as defined in claim 8 in which said shroud comprises a dome having top and bottom walls and having an annular side wall extending between said top and bottom walls, said side wall tapering inwardly upon progressing upwardly, said shroud further comprising an upright sleeve disposed within said dome and having an open upper end spaced below the top wall of said dome, said sleeve having an open lower end communicating with an opening in the bottom wall of said dome, and said sucking and blowing means comprising a fan disposed within said sleeve and further comprising a motor for rotating said fan about an upright axis.

11. Apparatus as defined in claim 10 in which said sleeve is spaced inwardly from the side wall of said dome, an a series of angularly spaced openings formed through said sleeve above said fan.

12. Apparatus as defined in claim 10 in which the lower side of the bottom wall of said dome is concave, the upper side of said bottom wall being convex.

13. Apparatus as defined in claim 8 further including means mounting said shroud for vertical adjustment relative to said vehicle, and power operated means for shifting said shroud vertically.

14. Apparatus as defined in claim 8 further including skirts depending from the left and right sides of said shroud and straddling the plants of said center row.

15. Apparatus as defined in claim 8 in which said conduits are made of flexible material and in which said manifolds are made of rigid material, said apparatus further including flexible pipes connected to the inboard ends of said manifolds and communicating with said chamber.

16. Apparatus as defined in claim 15 further including means connected to each manifold and mounting each manifold for vertical ajdustment relative to said shroud.

17. Apparatus as defined in claim 16 further including means connected to each manifold and mounting each manifold for horizontal swinging relative to said shroud whereby each manifold may be swung to a generally fore-and-aft extending transport position.

18. Apparatus as defined in claim 8 further including a valve in each of said conduits, each valve being selectively adjustable to vary the flow rate of air passing through the conduit.

* * * * *